(12) United States Patent
Miller et al.

(10) Patent No.: US 7,619,124 B2
(45) Date of Patent: Nov. 17, 2009

(54) PROCESS FOR THE PREPARATION OF PROPYLENE GLYCOL

(75) Inventors: Dennis J. Miller, Okemos, MI (US);
James E. Jackson, Haslett, MI (US);
Simona Marincean, DeWitt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 12/079,659

(22) Filed: Mar. 28, 2008

(65) Prior Publication Data

US 2008/0242898 A1 Oct. 2, 2008

Related U.S. Application Data

(60) Provisional application No. 60/920,727, filed on Mar. 29, 2007.

(51) Int. Cl.
*C07C 31/18* (2006.01)
*C07C 31/20* (2006.01)
(52) U.S. Cl. ...................................... 568/861; 568/862
(58) Field of Classification Search ................. 568/861, 568/862
See application file for complete search history.

(56) References Cited

U.S. PATENT DOCUMENTS 6,291,725 B1 9/2001 Chopade et al.
6,403,844 B1 6/2002 Zhang et al.

OTHER PUBLICATIONS

Dasari et al. Low-pressure hydrogenolysis of glycerol to propylene glycol. Applied Catalysis A: General, 2005, 281, pp. 225-231.*
Kovacs, D., D.J. Miller, and J.E. Jackson, "On the Mechanism of Catalytic Hydrogenation of Lactic Acid to Propylene Glycol," Paper #340, 221st ACS National Meeting, San Diego, CA, Apr. 2001.
Wainwright, M.S., T. Ahn, D.L. Trimm, "Solubility of Hydrogen in Alcohols and Esters," J. Chem. Eng. Data 1987, 32, 22-24.
Nagorski, R.W., J.P. Richard, "Mechanistic Imperatives for Aldose-Ketose Isomerization in Water: Specific, General Base- and Metal Ion-Catalyzed Isomerization of Glyceraldehyde with Proton and Hydride Transfer," J. Am. Chem. Soc. 2001, 123, 794-802.
Peereboom, L., B. Koenigsknecht, M. Hunter, J.E. Jackson, and D.J. Miller, "Aqueous Phase Adsorption of Glycerol and Propylene Glycol onto Activated Carbon," Carbon 2007, 45, 579-586.

* cited by examiner

*Primary Examiner*—Sikarl A Witherspoon
(74) *Attorney, Agent, or Firm*—Ian C. McLeod

(57) ABSTRACT

A process for the preparation of propylene glycol from glycerol by a high pressure and temperature hydrogenation reaction is described. In a particular embodiment, a base is present in the solvent mixture with an alkanol or ether of the alkanol. The reaction progresses over a transition metal catalyst. Propylene glycol is used for antifreeze and deicing compositions.

27 Claims, 6 Drawing Sheets

PROCESS FOR THE PREPARATION OF PROPYLENE GLYCOL

CROSS-REFERENCE TO RELATED APPLICATION

Priority is claimed to Provisional Application No. 60/920,727, filed Mar. 29, 2007, the entire disclosure of which is herein incorporated by reference.

STATEMENT REGARDING FEDERALLY SPONSORED RESEARCH OR DEVELOPMENT

Not Applicable

BACKGROUND OF THE DISCLOSURE

1. Field of the Disclosure

The present invention relates to a process for the preparation of a composition comprising propylene glycol from glycerol. In particular, the present invention relates to a hydrogenolysis process wherein glycerol is reacted with a transition metal catalyst at elevated pressures and temperatures in the presence of hydrogen and an alkanol containing 1 to 8 carbon atoms and a water solubilized alkali metal base, where the amount of water is preferably held to a minimum.

2. Brief Description of Related Technology

Propylene glycol, known also by the systematic name propane-1,2-diol, is an organic compound (a diol alcohol), usually a tasteless, odorless, and colorless clear oily liquid that is hygroscopic and miscible with water, acetone, and chloroform. Industrially, propylene glycol is most commonly produced by propylene oxide hydration. Different manufacturers use non-catalytic high-temperature process at 200-220° C. or catalytic route which proceeds at 150-180° C. in presence of ion exchange resin or small amounts of sulfuric acid or alkali. Typically, final products contain 20% 1,2-propanediol, 1.5% of dipropylene glycol and small amount of other polypropylene glycol. Pure propylene glycol can be obtained after rectification.

Industrial uses of propylene glycol include but are not limited to, moisturizers to maintain moisture in medicines, cosmetics, food, tobacco products, as a flavoring agent in Angostura and Orange bitters, as a solvent for food colors and flavorings, as a humectant food additive, labeled as E number E1520, as a carrier in fragrance oils, as a food grade antifreeze, in smoke machines to make artificial smoke for use in firefighters training and theatrical productions, in hand sanitizers, antibacterial lotions, and saline solutions, as a main ingredient in many cosmetic products, including baby wipes, bubble baths, and shampoos, as the primary ingredient in the "Paint" inside a Paintball, as a base ingredient in aircraft deicing fluid and some automobile antifreezes, and in cryonics.

U.S. Pat. No. 6,403,844 issued to Zhang et al. describes a process for condensed phase catalytic hydrogenation of lactic acid to propylene glycol. Particularly, it provides for a process for production of propylene glycol with high yield and selectivity in an aqueous reaction mixture of lactic acid and hydrogen with an essentially pure elemental ruthenium catalyst on an inert support at elevated pressure and temperature. Further still, it provides for a process wherein the catalyst is a ruthenium salt deposited on a microporous support, reduced to ruthenium on the support with hydrogen, and oxidized in the presence of oxygen to provide a ruthenium oxide surface on the surface of the ruthenium metal and wherein the catalyst is maintained in the surface oxidized state until it is reduced with hydrogen prior to the reaction process.

Glycerol is a chemical compound with the formula $HOCH_2CH(OH)CH_2OH$. This colorless, odorless, viscous liquid is widely used in pharmaceutical formulations. Also commonly called glycerin or glycerine, it is a sugar alcohol, and is sweet-tasting and of low toxicity. It is a central component of lipids.

Until recently, synthetic glycerol was mainly manufactured at an industrial scale from epichlorohydrin. Since glycerol forms the backbone of triglycerides, it is produced on saponification or transesterification. Soap-making and biodiesel production are respective examples. Glycerol is a 10% by-product of biodiesel production (via the transesterification of vegetable oils). This has led to a glut of crude glycerol in the market, making the epichlorohydrin process no longer economical. A great deal of research is being conducted to try to make value-added molecules from crude glycerol (typically containing 20% water and residual esterification catalyst) obtained from biodiesel production, as an alternative to disposal by incineration.

Accordingly, there exists a need for alternative propylene glycol production particularly from glycerol.

OBJECTS

It is an object of the present invention to increase conversion of glycerol to propylene glycol under hydrogenolysis conditions at relatively mild temperatures and pressures. It is also an object of the present invention to increase the selectivity towards propylene glycol. It is further an object of the present invention to decrease the yield of side reaction products, such as ethylene glycol and one-carbon compounds. It is finally an object of the present invention to decrease the amount of base needed in the reaction.

These and other objects will become increasingly apparent by reference to the following description and the drawings.

SUMMARY

The present disclosure provides for a process for the preparation of a composition comprising propylene glycol from glycerol which comprises: (a) reacting in a reaction mixture, glycerol, a hydrogen activated transition metal catalyst, hydrogen, a solvent and an alkali metal base in a closed reaction vessel at a temperature between about 180° C. and 220° C. and at a pressure between about 800 and 1500 psig; and (b) optionally separating the composition comprising the propylene glycol from the reaction mixture. The propylene glycol can be produced in at least a 50% conversion of glycerol. The solvent is selected from the group consisting of water, an alkanol containing 1 to 8 carbon atoms, an ether of the alkanol containing 1 to 8 carbon atoms and a mixture of water with either the alkanol or the ether. In a particular embodiment, the solvent is a mixture of water with an alkanol containing 1 to 8 carbon atoms in a mole ratio of alkanol to water between about 100 to 1 and 1 to 1. In an exemplary embodiment, the transition metal catalyst is supported on activated carbon and produced before step (a) by reduction with hydrogen of a passivated transition metal catalyst. The transition metal catalyst is selected from the group consisting of activated Ni/Re and Ru. In a particular embodiment, the alkanol is selected from the group consisting of ethanol, isopropanol and tert-butanol alcohol. In yet a further exemplary embodiment, the alkali metal base is a member selected from the group consisting of sodium hydroxide, sodium bicarbonate, potassium hydroxide, potassium hydrogen carbonate and mixtures thereof. Either Sodium hydroxide or potassium hydroxide can be provided in a concentration of between about 0.1 and 1.0 M per mole of glycerol. In a further embodiment, the catalyst is ruthenium metal as a sponge.

The present invention relates to a process for the preparation of a composition comprising more than 50% propylene glycol from glycerol which comprises: reacting in a reaction mixture, glycerol, a hydrogen activated transition metal catalyst, hydrogen, and a mixture of an alkanol containing 1 to 8 carbon atoms and water and an alkali metal base in a closed reaction vessel at a temperature between about 180° C. and 220° C. and at a pressure between about 800 and 1500 psig, wherein the mole ratio of alkanol to water is between about 100 to 1 and 1 to 1; and separating the composition comprising the propylene glycol from the reaction mixture.

In aqueous media, glycerol (GO), a low-cost renewables-based feedstock, can be catalytically converted under mild conditions to the commodity products propylene glycol (PG), lactic acid (LA) and ethylene glycol (EG). This invention discloses the use of catalysts, solvents, and reaction conditions aimed at optimizing selectivity towards PG and at the same time augmenting understanding of catalyst-substrate interactions.

The term "alkali metal" includes lithium, sodium, potassium, rubidium and cesium. The term "transition metal catalysts" includes the group 3 to 12 metals. Typically, the preferred transition metals are easily surface oxidized and are stable as metals for hydrogenolysis at the elevated temperatures and pressures in a closed reaction vessel.

The catalyst is preferably activated Ni/Re on activated carbon support, Ru on activated carbon support, or pure Ru metal as a porous sponge produced by reduction with hydrogen of surface oxide passivated metals. Most preferably, the alkanol is selected from the group consisting of ethanol, isopropanol and tert-butanol alcohol. The alkali metal bases are sodium hydroxide, sodium bicarbonate, potassium hydroxide or potassium hydrogen carbonate. In an exemplary embodiment, the alkali metal base is sodium hydroxide or potassium hydroxide at a concentration of between about 0.1 and 1.0 mole per mole of glycerol. Preferably, there is only a small amount of water present to dissolve the base. Water is generated in the reaction. Initial alkanol to water molar ratios of 1.5 to 1 and 100 to 1 for ethanol, 1 to 1 and 60 to 1 for isopropanol and 1 to 1 and 40 to 1 for tert-butanol are preferred. In general, the selectivity of the process is more than 50 mole percent to propylene glycol based upon the glycerol.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

Figure 1:
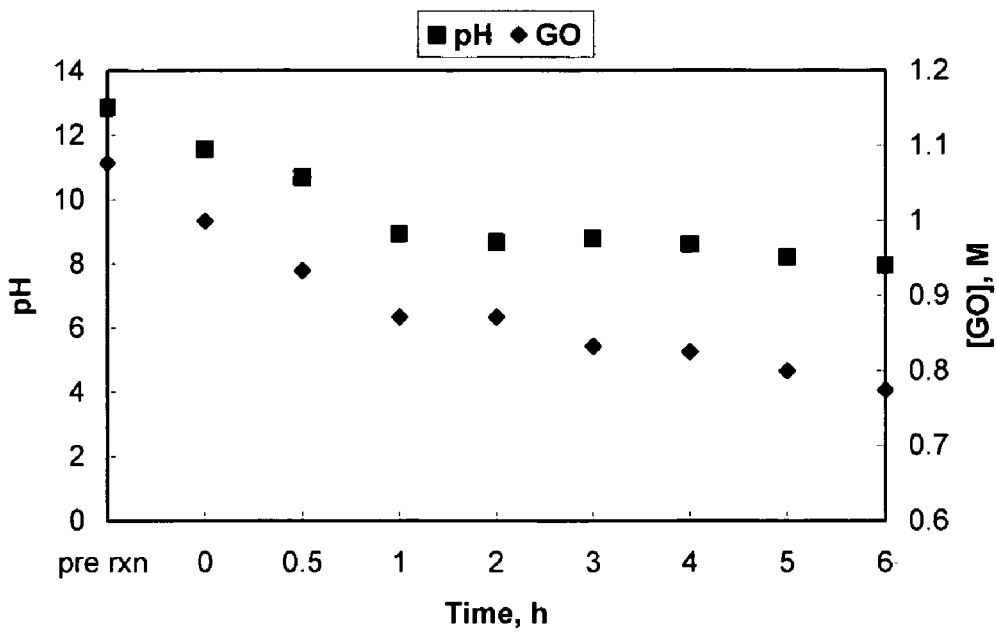
FIG. 1 is a graph showing glycerol (GO) concentration and solution pH as a function of time. The reaction was carried out on 100 ml solution of 1M GO and 0.1M KOH for 6 h in H2O at 200° C. and 1000 psig H2 using 0.5 g Ni/Re catalyst.

While the disclosed compositions and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The present disclosure provides for a process of producing propylene glycol (PG) from glycerol (GO). In particular, a process is provided that favors PG over other associated products such as ethylene glycol (EG) and one carbon compounds. Still further, the present disclosure provides for favorable conversion of GO to yield PG with little or no water in the reaction.

Figure 11:
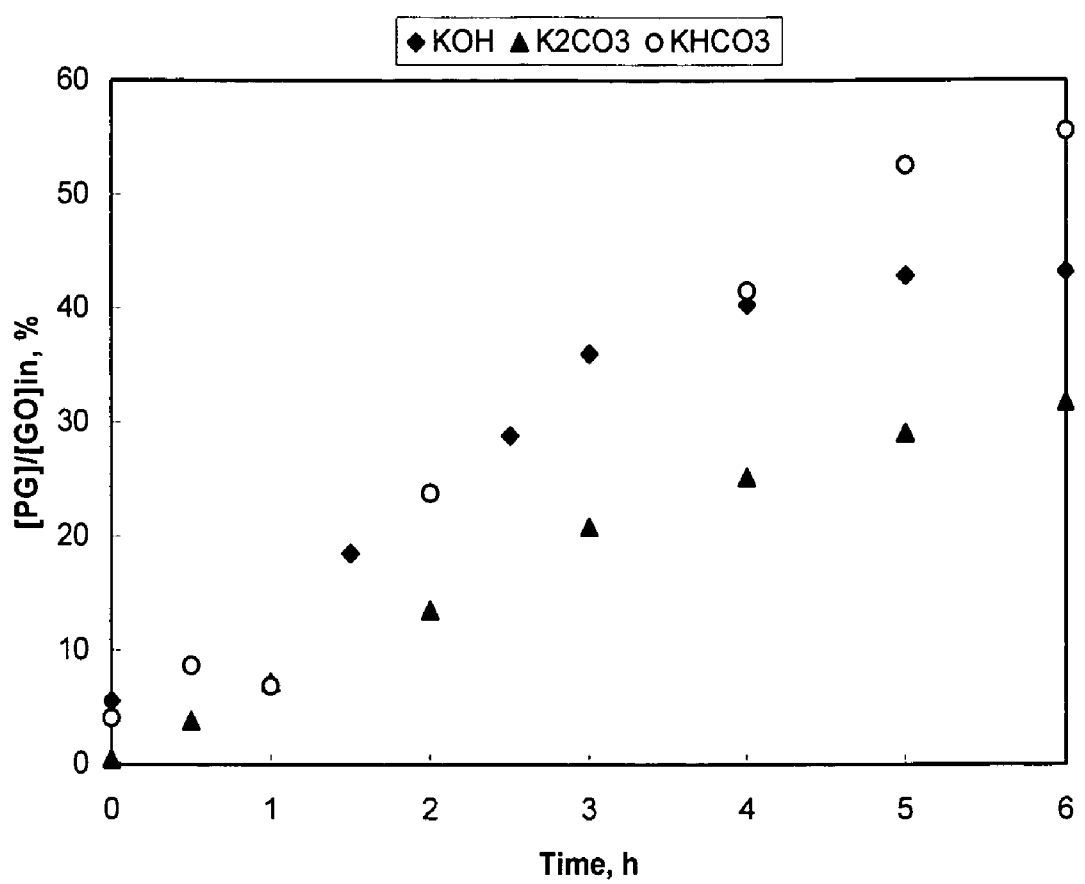
FIG. 11 is a graph showing PG yield on Ru/C with different bases in isopropanol. The reactions were carried out on 100 ml solution of 1M GO and 0.1M base for 4-6 h at 200° C. and 1000 psig H2.

In an exemplary embodiment, a process according to the present disclosure includes providing glycerol into a reaction over a transition metal catalyst on an inert support with hydrogen and a mixture of an alkanol or ether of the alkanol having 1-8 carbon atoms, water and an alkali metal base. Typically the reaction is performed at relatively elevated temperatures and pressures. In a particular embodiment, 100 ml solution of 1M GO and a 0.1M $KHCO_3$ in isopropanol over an Ru/C catalyst for 4-6 hours at 200° C. and 1000 psig $H_2$. As shown in FIG. 11, this process results in an over 50% yield of PG.

Preparing an operable catalyst is described in U.S. Pat. No. 6,291,725 issued to Chopade et al., the subject matter of which is hereby incorporated by reference in its entirety for all purposes. In an exemplary embodiment, the catalyst according to U.S. Pat. No. 6,291,725 is prepared through a process of providing the selected transition metal salt in a solvent, preferably water; providing an inert support in the solvent for the salt to be deposited on the support and then evaporating the solvent, reducing the metal salt to the active metal with hydrogen; passivating the active metal with oxygen and then rereducing the oxygenated metal catalyst with hydrogen prior to reaction. The passivating step makes operable handling of the catalyst without using elaborate storage conditions. In an exemplary embodiment, the inert support can be activated or microporous carbon, titania, or alumina. In a further embodiment, the catalyst is a ruthenium-based metal catalyst. The amount of ruthenium metal deposited on the carbon support can range from about 1.5 to 5.0 wt %.

In an exemplary embodiment, the method for preparing a particular catalyst comprises the steps of (1) depositing the ruthenium salt in water on the carbon support, (2) drying to deposit the ruthenium salt onto the carbon surface, (3) reducing the ruthenium salt to the ruthenium metal with hydrogen, and (4) passivating the catalyst with oxygen to produce a layer of ruthenium oxide on surfaces of the ruthenium metal. The oxidation passivates or stabilizes the catalyst and can be achieved by passing a stream of oxygen over the catalyst. In a particular embodiment, the oxygen stream is comprised of 2% oxygen in an inert gas such as argon. The oxidized catalyst can be stored under atmospheric conditions without a significant loss of catalytic activity. The catalyst is re-reduced with hydrogen prior to the conversion reaction.

EXAMPLES

The following Examples illustrate the disclosed compositions and methods, but are not intended to limit the scope of any claims thereto.

Example I

The present disclosure relates generally to a process for generating propylene glycol from glycerol. In particular, the present disclosure provides for a process that favors propylene glycol in a greater than 50% yield by hydrogenolysis of glycerol over a hydrogen activated transition metal catalyst with a mixture of an alkanol or ether of the alkanol, water and an alkali metal base under a suitable temperature and pressure and molar ratio of alkanol to water. The reaction is performed in a closed reaction vessel. In an exemplary embodiment, the alkanol contains 1 to 8 carbon atoms and the ratio of alkanol to water is between 100:1 to 1:1. In a further embodiment, the reaction is performed at a temperature between about 180 to 220° C. and at a pressure between about 800 and 1500 psig.

The Ni/Re/C catalyst contains 2.5 wt % Ni and 2.5 wt % Re on activated carbon. Reactions were run in a Parr stirred autoclave (Model 4561) at 1000 psi $H_2$ and 200° C. for 6 h. A weighed quantity (0.5 g dry basis) of the catalyst was introduced into the reactor and reduced at 280° C. and 500 psi $H_2$ (Ni/Re/C) for 13 hours. After cooling, 100 ml of solution (1.0M GO and 0.1-1.0M KOH) was added to the closed reactor. For reactions in solvent mixtures, (Exp. # 6, 7, 8, and 9 in Table 2), the water/solvent ratio was 1/9 (v/v). When the solvent was either t-BuOH or 1,4-dioxane, 1.5 g of water was added to the solution to facilitate dissolution of KOH, because of its low solubility in these solvents. Once reaction temperature was achieved and the reaction vessel pressurized, samples were taken at 30 minute intervals for the first hour, and then hourly, and analyzed via HPLC. The HPLC column was a BIORAD Aminex HPX-87H run at 65° C. with 5 mM $H_2SO_4$ as the mobile phase at a flow rate of 0.6 ml/min, using both UV (210 nm) and refractive index (RI) detection.

Quantitative evaluation of feed conversion and product distribution, given in Tables 1 and 2, were based on HPLC analyses after 6 h reaction time for most reactions. In several cases, evaluation is based on the sample taken at 5 hr. Selectivity is defined as mol product formed/mol glycerol converted and yield is mol product formed/mol initial glycerol. The carbon balance is defined as:

$$C\ Balance\ (\%)=\{[GO]+[PG]+[EG]+[LA]\}_{final}/[GO]_{initial} \times 100$$

The number of carbon atoms were not explicitly accounted for because all compounds have the same number of carbons except EG. In the case of EG, for each molecule of EG formed there is a corresponding one-carbon compound formed as well.

In reaction, time t=0 is defined as the point when reaction conditions have reached 200° C. and the reaction vessel is pressurized with $H_2$. Hence, for the solvents i-PrOH or t-BuOH there is PG in the reaction mixture at t=0 because of reaction during the 15 minute heat up. A control experiment in which base was added to the reaction mixture only after heating to 200° C. showed no PG at t=0. Two catalysts were evaluated, Ni/Re on carbon and Ru on carbon: Ni/Re on carbon was more active and selective than Ru on carbon for GO hydrogenolysis to PG. Partial replacement of water with other hydroxylic solvents such as simple alcohols increased the selectivity and conversion in the order of: ethanol/water <water <2-propanol/water~tert-butanol/water. The unmixed solvents yield the following trend: water <ethanol <isopropanol <tert-butanol, with a three-fold increase in PG yield in tert-butanol relative to water.

The distribution of GO hydrogenolysis products, PG, Lactic Acid (LA) and EG in water is influenced by the catalyst used and the amount of base present in the reaction mixture (Table 1 and Table 2).

TABLE 1

| | | | GO Hydrogenolysis in Aqueous Medium[a] | | | | |
|---|---|---|---|---|---|---|---|
| Exp. | Catalyst | KOH(M) | Conv(%) | Selectivity(%) PG | Selectivity(%) LA | Selectivity(%) EG | Carbon Balance(%) |
| 1 | Ni/Re | 1.00 | 99 | 64 | 21 | 6 | 92 |
| 2 | Ni/Re | 0.5 | 74 | 44 | 36 | 9 | 92 |
| 3 | Ni/Re | 0.25 | 43 | 46 | 31 | 7 | 93 |
| 4 | Ni/Re | 0.10 | 23 | 61 | 22 | 7 | 98 |

[a]Reactions carried out on 100 ml samples of 1 M GO for 6 h in $H_2O$ at 200° C. and 1000 psig $H_2$ using 0.5 g catalyst.

The C—C cleavage pathway that leads to EG takes place to a small extent in the presence of Ni/Re, when keto-enol tautomerization is favored as is shown by the high sensitivity of the reaction to the amount of base. GO consumption rate closely follows the solution pH, slowing greatly when the reaction medium becomes close to neutral (FIG. 1). The acids identified in the reaction mixture, formic and lactic, are not present in high enough quantities to account entirely for the pH decrease (e.g. to neutralize all base present). Formic acid (as formate) is produced via either Cannizzaro reaction of formaldehyde, a byproduct in the retro-aldol cleavage pathway, with itself or with other aldehydes, or via oxidation of formaldehyde leading to a maximum formic acid: EG molar product ratio of 1:1. The actual detected ratio of formic acid to EG was 0.13. Control experiments with 1.0M formic acid in 0.1M KOH solution over Ru/C showed that base present is neutralized, but the free acid is degraded completely over 6 h, without detection of other one-carbon compounds in the reaction solution. It is suspected that $CO_2$ is formed via degradation of formic acid and is present in solution as carbonic acid or bicarbonate, which contributes to the pH decrease. However, carbonate was not detected via HPLC even though standard carbonate solutions do show a peak. The preparation of HPLC samples, involving neutralization in the acidic mobile phase (5 mM $H_2SO_4$), may lead to acidification of the solution and thus, loss of carbonic acid via $CO_2$ evolution.

In order to understand the mechanism of GO hydrogenolysis in heterogeneous conditions, it is helpful to gain insight into the interactions that take place between the catalyst and the reactants on one hand and catalyst and the solvent on the other hand. Under particular reaction conditions, the Ru/C catalyst is capable of exchanging hydrogen between $D_2O$ and molecular $H_2$, presumably via exchange of H and OD sites bound to the surface of the catalyst (Kovacs, D., D. J. Miller, and J. E. Jackson, "On the Mechanism of Catalytic Hydrogenation of Lactic Acid to Propylene Glycol," Paper #340, 221 st ACS National Meeting, San Diego, Calif., April 2001). Being an avid hydrogen bonder, water may also agglomerate at the surface of the catalyst around the metal centers. Other OH-bearing compounds should similarly be able to participate in such an interaction as long as the OH has access to the surface of the catalyst, i.e. is not sterically hindered. So water and GO may be competitors for catalytically relevant sites. At the same time, the catalyst support carbon is hydrophobic and GO and reaction products, with their carbon backbones, should be favored over water to absorb in the carbon pore structure. Thus, species concentrations within the carbon pores may be significantly different, particularly in terms of water, than those in the bulk solution, and this may strongly affect reaction rates.

To further investigate hydrogen bonding and hydrophobicity as driving forces for the reaction, water was partially (water/solvent ratio 1/9 (v/v)) replaced with compounds similar to GO in that they possess OH groups and a carbon backbone.

Figure 2:
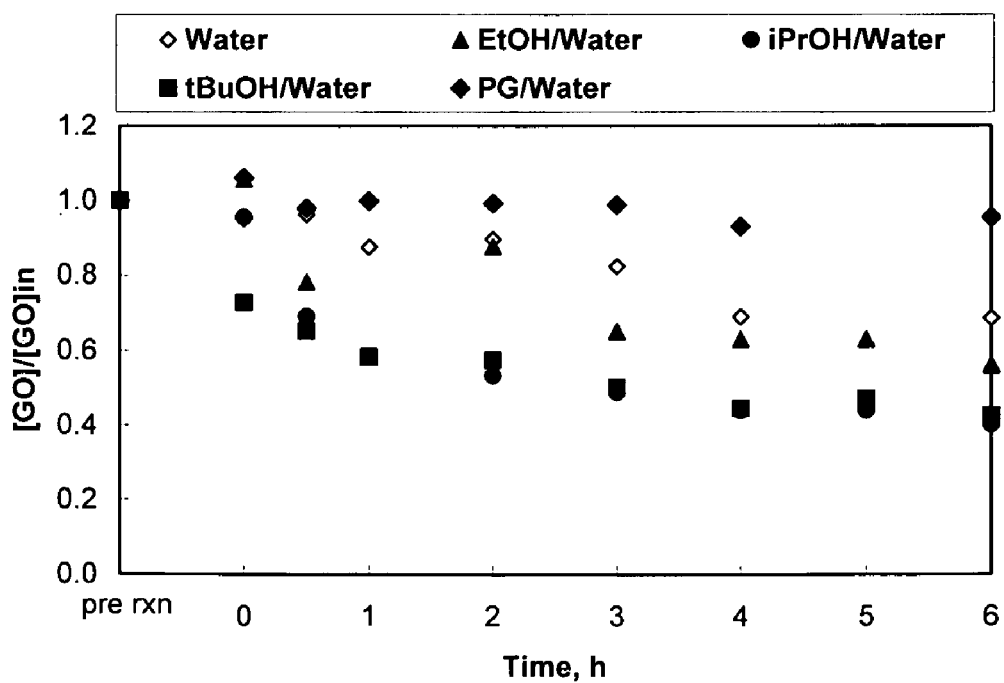
FIG. 2 is a graph showing the GO normalized concentration as a function of time in solvent/water mixtures. The reactions were carried out on 100 ml solution of 1M GO and 0.1M KOH for 4-6 h at 200° C. and 1000 psig H2 using 0.5 g Ni/Re catalyst.

The GO conversion (FIG. 2) increased in the order:

PG<water<EtOH<$i$-PrOH~$t$-BuOH.

Figure 3:
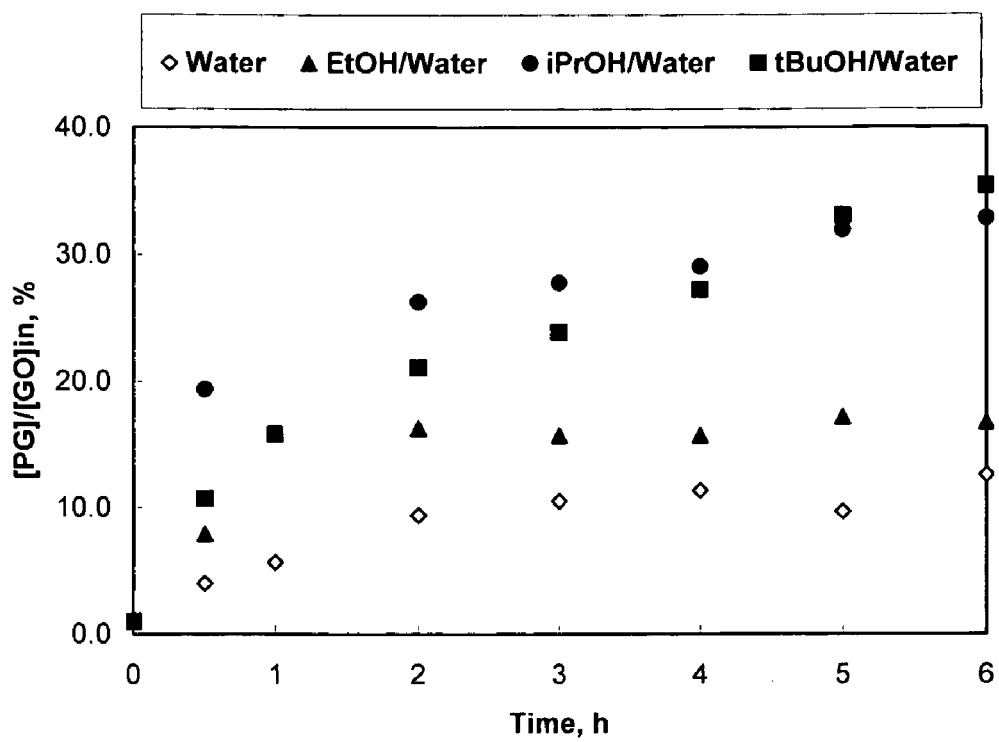
FIG. 3 is a graph showing the PG yield in solvent/water mixtures. The reactions were carried out on 100 ml solution of 1M GO and 0.1M KOH for 6 h at 200° C. and 1000 psig H2 using 0.5 g Ni/Re catalyst.

The initial GO conversion rate is several times larger in i-PrOH/water and t-BuOH/water than in just water. The PG yield (FIG. 3) shows the same trend. Solvents of i-PrOH/water and t-BuOH/water mixtures have very similar effects on the GO conversion and PG yield, which shows that the reaction is more sensitive to the presence of —OH than to the increase in the carbon backbone size, given that both mixtures included the same amount of water. Tert-butanol has a carbon backbone similar in size to that of GO, but its hydroxyl site is much more shielded by the large, hydrophobic t-butyl group. The low GO reactivity in PG/water is a strong indicator of PG inhibition.

The product distribution is affected by the solvent environment. While PG obtained as hydrogenation of pyruvaldehyde takes place, LA is formed via a hydride transfer from hydrated pyruvaldehyde. PG should be favored at the expense of LA as the polarity of the reaction medium decreases, and indeed their respective selectivities vary in opposite directions (Table 2).

Lower GO conversion rates in water can be the result of several factors and/or conditions. If GO is competing for absorption sites on the catalyst surface with solvents, it may do so more successfully against i-PrOH and t-BuOH than against water because the —OH groups in GO are all less shielded than the ones in i-PrOH and t-BuOH. This is further supported by the low lactic acid yields in the presence of these alcohols, suggesting that water (a strong competitor) is not present in the vicinity of the catalyst in alcohol solvent. Still further, the presence of PG clearly reduces reaction rate—water may be ineffective in removing product PG from the reaction environment, whereas alcohols may preferentially displace PG from the carbon pore structure. Moreover, water is a poor solvent for hydrogen, as hydrogen solubility in water is only 20 to 30% that in simple alcohols (Wainwright, M. S., T. Ahn, D. L. Trimm, "Solubility of Hydrogen in Alcohols and Esters," J. Chem. Eng. Data 1987, 32, 22-24).

Figure 4:
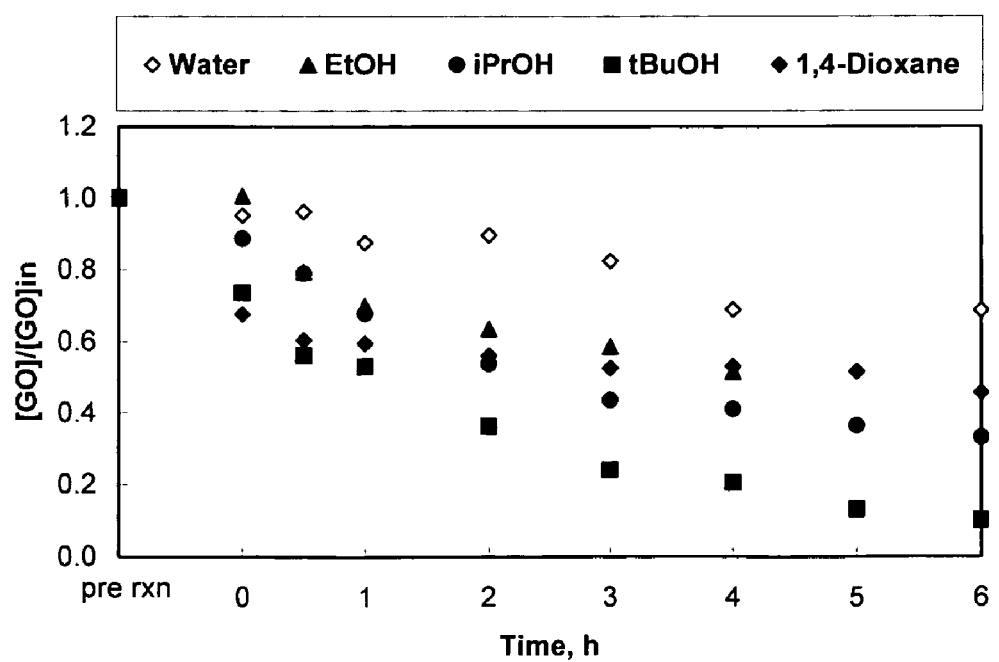
FIG. 4 is a graph showing the GO normalized concentration as a function of time in organic solvents. The reactions were carried out on 100 ml solution of 1M GO and 0.1M KOH for 4-6 h at 200° C. and 1000 psig H2 using 0.5 g Ni/Re catalyst.
Figure 5:
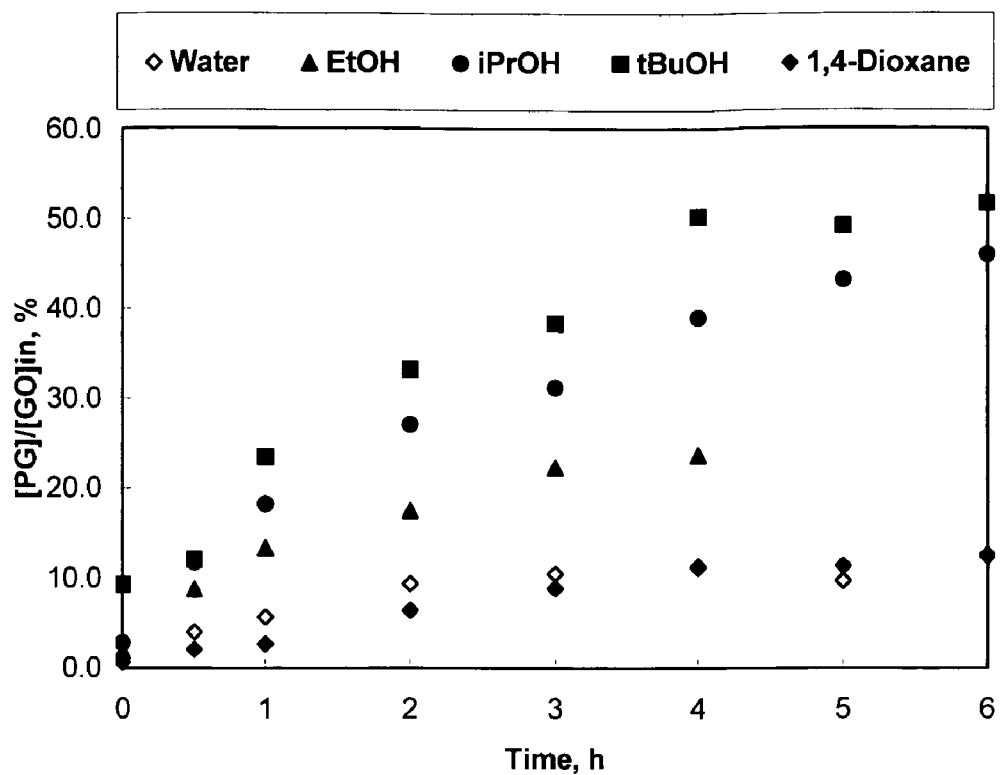
FIG. 5 is a graph showing the PG yield in organic solvents. The reactions were carried out on 100 ml solution of 1M GO and 0.1M KOH for 4-6 h at 200° C. and 1000 psig H2 using 0.5 g Ni/Re catalyst.

Full replacement of water with organic solvents leads to further increases in the GO conversion and PG yield in the order:

water<EtOH<$i$-PrOH<$t$-BuOH (FIGS. 4 and 5).

As can be seen from Table 2, GO conversion almost doubles going from EtOH to t-BuOH, and yield of PG (FIG. 5) increases with conversion. Yet PG selectivity only increases modestly, while at the same time the LA and EG selectivities decrease. These experimental observations show that while the pathway for LA formation becomes less important because little water is present, presumably aldol reactions remain accessible. Glyceraldehyde, the first intermediate of GO hydrogenolysis, is known to be very reactive towards aldol condensation in basic medium (Nagorski, R. W., J. P. Richard, "Mechanistic Imperatives for Aldose-Ketose Isomerization in Water: Specific, General Base- and Metal Ion-Catalyzed Isomerization of Glyceraldehyde with Proton and Hydride Transfer," J. Am. Chem. Soc. 2001, 123, 794-802). The lower carbon balances may be due to the reactivity of the carbonyl compounds formed as intermediates toward condensation reactions, resulting in large molecular weight unsaturated compounds that colored the reaction samples.

TABLE 2

Go Hydrogenolysis in Different Solvents[a]

| Exp. | Solvent | Conv(%) | Selectivity(%) PG | Selectivity(%) LA | Selectivity(%) EG | Carbon Balance(%) |
|---|---|---|---|---|---|---|
| 5 | Water | 23 | 61 | 27 | 8 | 99 |
| 6 | EtOH/Water | 34 | 57 | 16 | 10 | 94 |
| 7 | i-PrOH/Water | 60 | 55 | 8 | 9 | 83 |

TABLE 2-continued

Go Hydrogenolysis in Different Solvents[a]

| Exp. | Solvent | Conv(%) | Selectivity(%) PG | Selectivity(%) LA | Selectivity(%) EG | Carbon Balance(%) |
|---|---|---|---|---|---|---|
| 8 | t-BuOH/Water | 58 | 62 | 8 | 8 | 87 |
| 9 | PG/Water | 11 | n/a | 46 | 9 | 95 |
| 10 | EtOH | 51 | 45 | 6 | 8 | 79 |
| 11 | i-PrOH | 67 | 69 | 3 | 9 | 88 |
| 12 | t-BuOH[b] | 90 | 58 | 1 | 6 | 69 |
| 13 | 1,4-Dioxane[b] | 55 | 23 | 0 | 14 | 66 |

[a]Reactions carried out for 4-6 h at 200° C. and 1000 psig $H_2$ using 0.5 g Ni/Re catalyst, 0.1 M KOH, and 1.0 M GO.
[b]1.5 g water was added to the reaction solution to enhance KOH solubility.

The experiment with 1,4-dioxane as solvent was characterized by poor solubility of GO and KOH into the solvent, hence water was added to the initial mixture. The absence of the hydroxyl functionality in the solvent decreased the system's reactivity.

Figure 6:
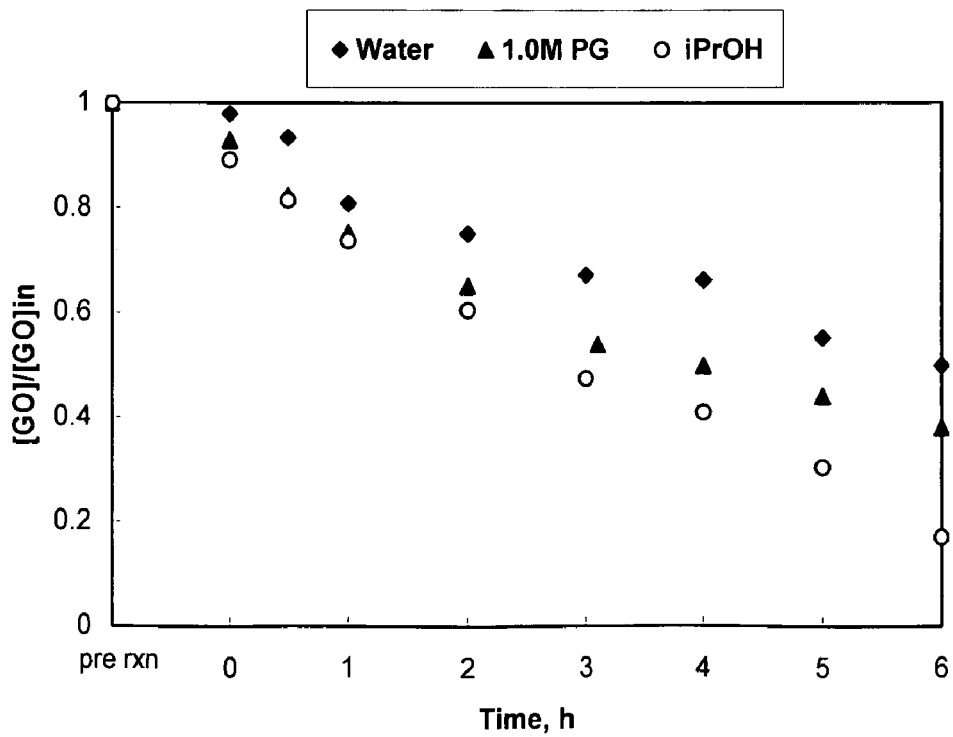
FIG. 6 is a graph showing GO normalized concentration with Ru/C at 0.25M KOH in water, PG-water mixture, and isopropanol. The reactions were carried out on 100 ml solution of 1M GO and 0.1M KOH for 4-6 h at 200° C. and 1000 psig H2.

Pyruvaldehyde conversion to LA is base-catalyzed while hydrogenation of pyruvaldehyde to PG is not. Thus, the influence of solvent on basicity of solution can be considered an additional factor in the observed differences in reactivity. From control experiments, it was learned that without base, GO hydrogenolysis in water does not take place. In FIG. 6, it is seen that increasing KOH concentration from 0.1 to 0.25M in water resulted in PG yield increasing from 13% to 25%, while similar experiments in i-PrOH/water solvent with KOH concentration increasing from 0.05 to 0.1M led to PG yields of 16% and 33%—a similar increase. In contrast, for 0.1M KOH the increase in PG yield from water to i-PrOH/water to i-PrOH is 13% to 45%. Thus, although it is possible that base strength plays a role in different solvents, solvent structure appears to have a larger effect.

These examples make reference to using KOH as the exemplary base. Experiments were performed using NaOH and it was determined that these bases are substantially interchangeable. Results using NaOH were substantially the same as those illustrated in the examples using KOH. Thus, a suitable base can be selected on a cost basis as between KOH and NaOH.

It is noted that carbon balance closures are generally poorer in the alcohols than in water. A control experiment in which the entire reaction was carried out without sample collection, and another in which reactor and contents were carefully weighed at each stage of reaction, showed no difference in recovery, indicating that product loss from the reactor is not a factor. Gas formation was measured in the reactor headspace and found <1% of initial carbon present as gaseous products, primarily methane. Control experiments with PG as starting material showed up to 80% conversion of PG under reaction conditions in i-PrOH, indicating accelerated product degradation in the alcohol solvent. It is possible that glycerol and alcohols were forming ethers at the elevated reaction temperatures, and that these ethers were not detected in HPLC.

Catalysts can be used with and without carbon support. In an exemplary embodiment, the reaction conditions can be used in a trickle-bed reactor set up. Absorption studies on the catalyst can be easily used on the products and reagents on different catalysts.

Example II

Experiments with Ru Sponge, Ru/C in Solvents (iPrOH, 1.0M PG)

Comparison between a carbon supported catalyst and an unsupported catalyst was done using Ru/C and Ru sponge. A 2.5 g Ru sponge was used in order to have the same metal surface area. The reactions were run with 0.25M KOH. Ru sponge appeared to be more active towards GO and also the PG yield was slightly higher than the one corresponding to the experiment in which the catalyst was Ru/C, when the solvent was water.

Figure 7:
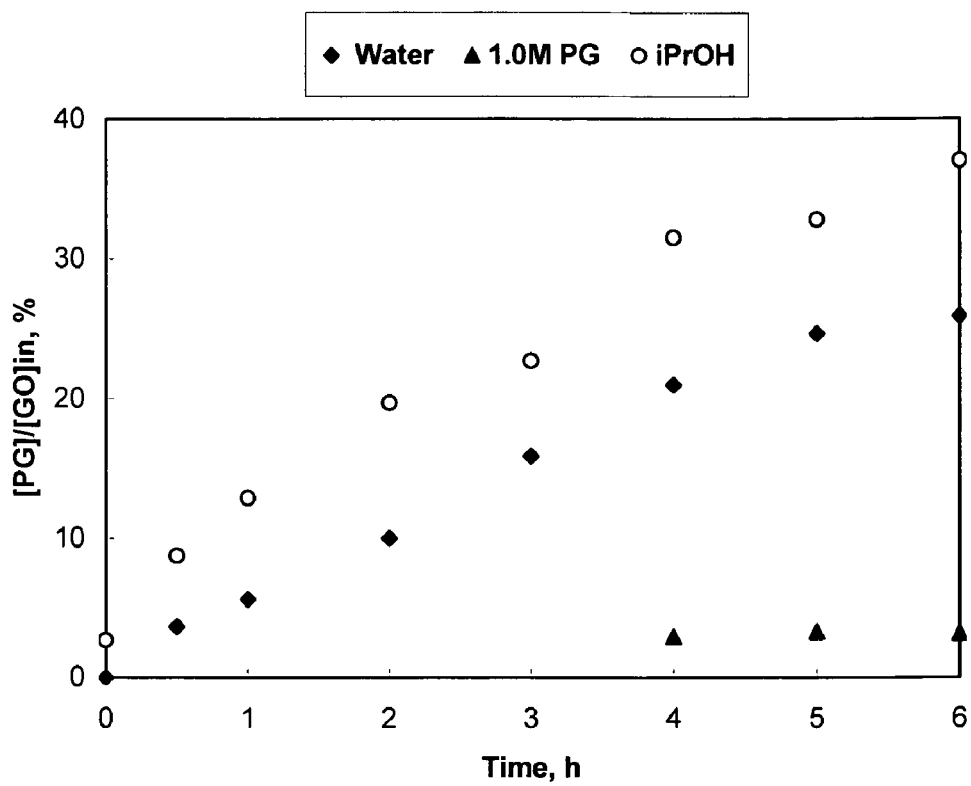
FIG. 7 is a graph showing PG yield for Ru/C at 0.25M KOH in water, PG-water mixture, and isopropanol. The reactions were carried out on 100 ml solution of 1M GO and 0.1M KOH for 4-6 h at 200° C. and 1000 psig H2.

Ru/C showed a behavior similar to the Ni/Re/C in that iPrOH as solvent increased the GO conversion and PG yield compared to water, FIGS. 6 and 7. Also, the carbon balance was lower in iPrOH (67%), than in water (99%). Control experiments regarding PG degradation, showed that when subjected to the reaction conditions (1.0M PG solution, 0.25M KOH, 200° C., 1000 psig $H_2$), PG degrades up to 30% in water and 80% in iPrOH.

Figure 8:
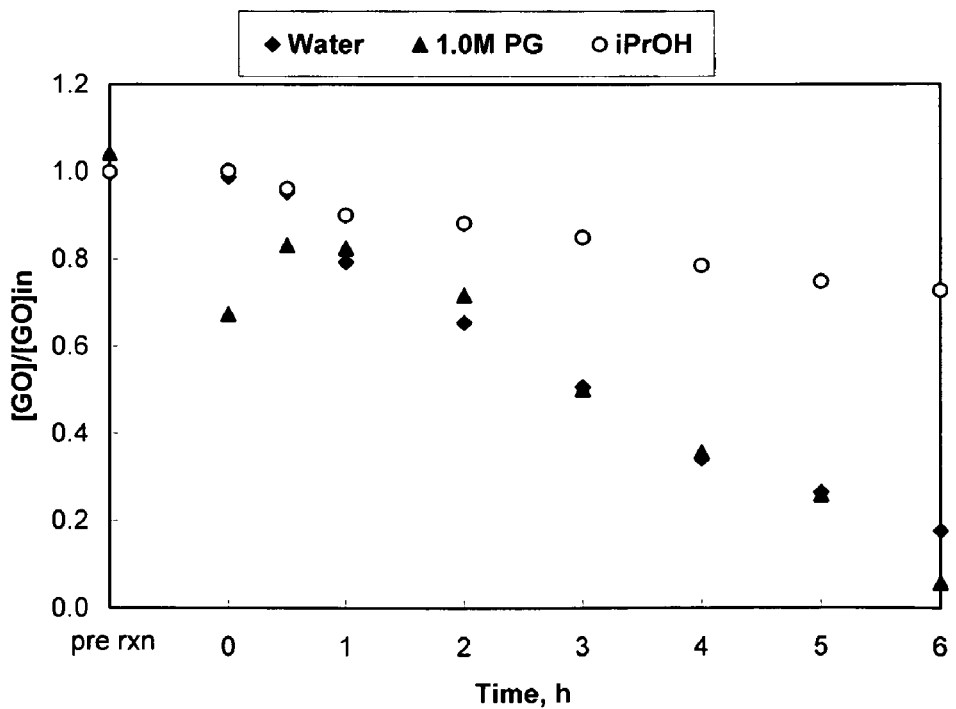
FIG. 8 is a graph showing GO normalized concentration with Ru sponge at 0.25M KOH in water, PG-water mixture, and isopropanol. The reactions were carried out on 100 ml solution of 1M GO and 0.1M KOH for 4-6 h at 200° C. and 1000 psig H2.

Experiments run in presence of 1.0M PG showed that, in the case of the Ru/C the reaction was basically turned off. That was not the case for Ru sponge, which gave a similar GO conversion and PG yield as in absence of PG (FIG. 8). This result suggests that when the structure of the catalyst consists of a carbon support besides the metal, GO and PG compete for the sites. It was shown that PG absorbs better than GO on carbon support from separate studies (Peereboom, L., B. Koenigsknecht, M. Hunter, J. E. Jackson, and D. J. Miller, "Aqueous Phase Adsorption of Glycerol and Propylene Glycol onto Activated Carbon," Carbon 2007, 45, 579-586). When the catalyst is Ru sponge (i.e. no carbon support), GO hydrogenolysis is not affected by PG presence since PG adsorbs less strongly than GO on Ru sponge.

Figure 9:
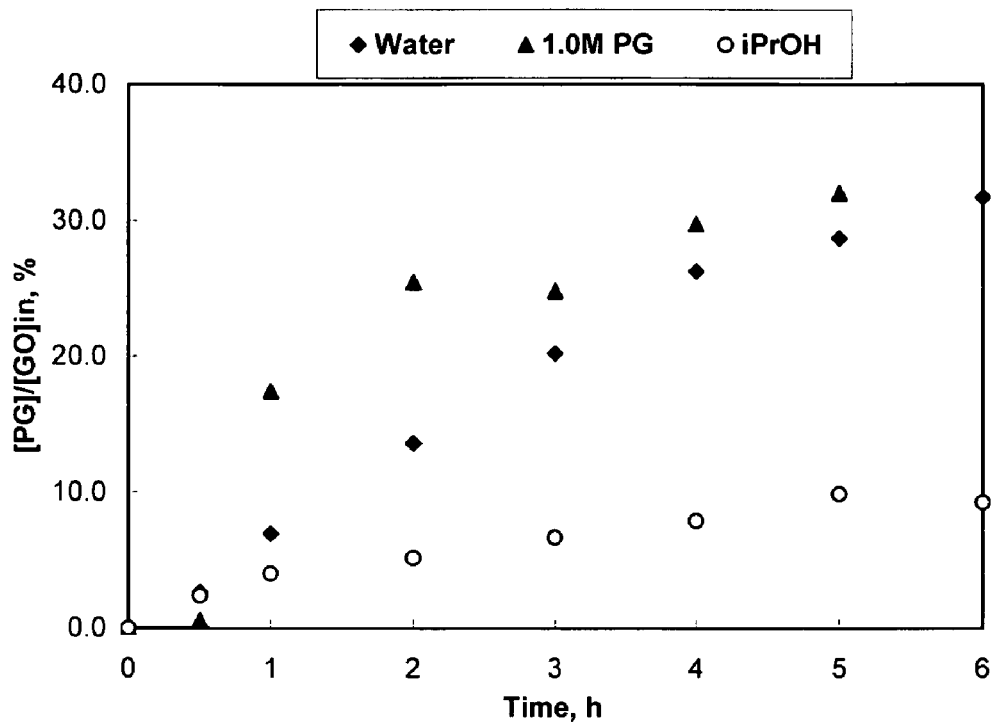
FIG. 9 is a graph showing PG yield with Ru sponge in water, PG-water mixture, and isopropanol. The reactions were carried out on 100 ml solution of 1M GO and 0.1M KOH for 4-6 h at 200° C. and 1000 psig H2.

The reaction in iPrOH was enhanced in terms of GO conversion and PG yield in the presence of Ru/C but turned off (reaction proceeded albeit more slowly) when Ru sponge was the catalyst as seen from FIG. 9. This may have happened as a result of GO, PG and iPrOH having similar affinities for Ru sponge rather then a matter of stability in the reaction conditions. Generally, iPrOH is more stable than GO in the presence of Ru sponge. Also when the reaction was run in iPrOH, GO and iPrOH concentrations were 1.0 and 12 M respectively, therefore more iPrOH was available than GO.

Several reactions with Ru/C catalyst were run at lower concentrations (0.25M GO and 0.05-0.06 M base using as iPrOH solvent). With dilution of both GO and KOH concentrations, the carbon balance increased dramatically from 67% to 91%. It is possible that the side reaction is aldol, i.e. bimolecular, and the products cannot be hydrogenated to polyols and therefore they are not detected by HPLC.

Example III

Effect of Different Bases in iPrOH as Reaction Medium

Figure 10:
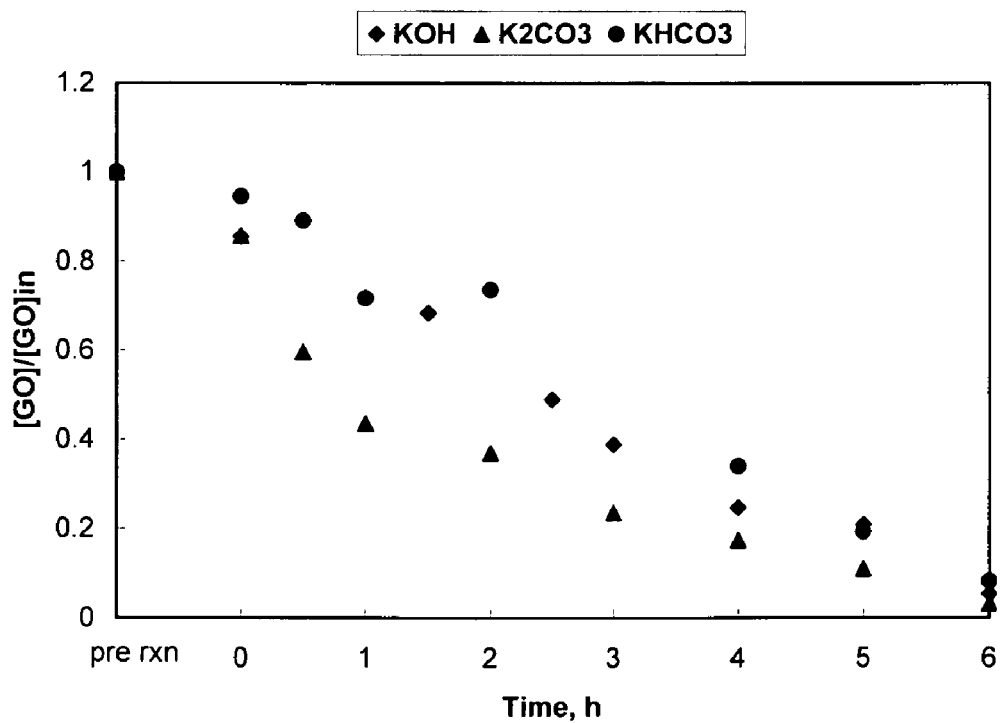
FIG. 10 is a graph showing GO normalized concentration on Ru/C and different bases in isopropanol. The reactions were carried out on 100 ml solution of 1M GO and 0.1M base for 4-6 h at 200° C. and 1000 psig H2.

When testing the effects of different bases in the alkanol solvent, it was observed that GO conversion was similar for all three base situations (i.e., $KHCO_3$, KOH and $K_2CO_3$) as shown in FIG. 10. PG yield decreased in the order:

$KHCO_3 > KOH > K_2CO_3$ (FIG. 11)

The results showed that $K_2CO_3$ was the worst alternative with very poor carbon balances. The bases were stronger in iPrOH. $KHCO_3$ was the least soluble from the set and one explanation for the observed results may be that it is the strongest and delivered in very small amounts to the reaction solution, where it came into contact with the reactants.

Given the low solubility of $KHCO_3$ in iPrOH the experiment was repeated while the reaction vessel was charged with both the base and the catalyst before reduction of the catalyst. The GO/iPrOH mixture was then added afterwards. The results were very similar with the previous run. These results can be seen below with respect to Table 3 and Table 4.

TABLE 3

GO Hydrogenolysis in Solvents Mixtures with 0.25 M KOH

| | | | | Selectivity (%)  | | | C Bal. |
|---|---|---|---|---|---|---|---|
| React. | Cat. | Solvent | Conv (%) | PG | LA | EG | (%) |
| 14 GO | Ru/C | Water | 50 | 52 | 18 | 18 | 99 |
| 15 GO | Ru/C | iPrOH | 84 | 44 | 9 | 9 | 67 |
| 16 GO | Ru/C | 1.0 M PG/Water | 62 | 27 | 5 | 16 | 85 |
| 17 GO | Ru sponge | Water | 82 | 39 | 12 | 12 | 70 |
| 18 GO | Ru sponge | iPrOH | 27 | 34 | 27 | 18 | 94 |
| 19 GO | Ru sponge | 1.0 M PG/Water | 75 | 43 | 17 | 6 | 93 |
| 20 PG | Ru/C | water | 35 | | 12 | 12 | 79 |
| 21 PG | Ru/C | iPrOH | 84 | | 11 | | 33 |

TABLE 4

GO Hydrogenolysis with Different Bases on Ru/C in iprOH[a]

| Base | Conc M | Conv (%) | Selectivity (%) | | | C Bal. (%) |
|---|---|---|---|---|---|---|
| | | | PG | LA | EG | |
| KOH | 0.06 | 79 | 54 | 11 | 21 | 91 |
| K2CO3 | 0.06 | 97 | 33 | 3 | | 34 |
| KHCO3 | 0.05 | 92 | 61 | 11 | 19 | 96 |

[a]GO concentration is 0.25 M

The present disclosure provides for a process of propylene glycol production from glycerol. Particular advantages associated with the exemplary embodiments set forth herein include but are not limited to: (a) higher conversion of glycerol to propylene glycol; and (b) reduced amounts of side products such as lactic acid, and ethylene glycol. Accordingly, the foregoing description is given for clearness of understanding only, and no unnecessary limitations should be understood therefrom, as modifications within the scope of the disclosure may be apparent to those having ordinary skill in the art.

Throughout the specification, where the compositions, processes, or apparatus are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

What is claimed is:

1. A process for the preparation of a composition comprising propylene glycol from glycerol which comprises:
    (a) reacting in a reaction mixture, glycerol, a hydrogen activated transition metal catalyst, hydrogen, a solvent, and an alkali metal base in a closed reaction vessel at a temperature between about 180° C. and 220° C. and at a pressure between about 800 and 1500 psig; and
    (b) optionally separating the composition comprising the propylene glycol from the reaction; and
    wherein the propylene glycol is produced with at least a 50% molar conversion of glycerol.

2. The process of claim 1 wherein the solvent is selected from the group consisting of water, an alkanol containing 1 to 8 carbon atoms, an ether of the alkanol containing 1 to 8 carbon atoms and a mixture of water with either the alkanol or the ether.

3. The process of claim 1 wherein the solvent is a mixture of water with an alkanol containing 1 to 8 carbon atoms in a mole ratio of alkanol to water between about 100 to 1 and 1 to 1.

4. The process of claim 1 wherein the transition metal catalyst is supported on activated carbon and produced before step (a) by reduction with hydrogen of a passivated transition metal catalyst.

5. The process of claim 4 wherein the transition metal catalyst is selected from the group consisting of activated Ni/Re and Ru.

6. The process of claim 3 wherein the alkanol is selected from the group consisting of ethanol, isopropanol and tert-butanol alcohol.

7. The process of claim 1 wherein the alkali metal base is selected from the group consisting of sodium hydroxide, sodium bicarbonate, potassium hydroxide, potassium hydrogen carbonate and mixtures thereof.

8. The process of claim 1 wherein the alkali metal base is sodium hydroxide at a concentration of between about 0.1 and 1.0 M per mole of glycerol.

9. The process of claim 1 wherein the alkali metal base is potassium hydroxide at a concentration of between about 0.1 and 1.0 M per mole of glycerol.

10. The process of claim 1 wherein the catalyst is ruthenium metal as a sponge.

11. A process for the preparation of a composition comprising more than 50% propylene glycol from glycerol which comprises:
    (a) reacting in a reaction mixture, glycerol, a hydrogen activated transition metal catalyst, hydrogen, and a mixture of an alkanol or ether containing 1 to 8 carbon atoms and water and an alkali metal base in a closed reaction vessel at a temperature between about 180° C. and 220° C. and at a pressure between about 800 and 1500 psig, wherein the mole ratio of alkanol or ether to water is between about 100 to 1 and 1 to 1; and (b) optionally separating the composition comprising the propylene glycol from the reaction; and wherein the propylene glycol is produced with at least a 50% molar conversion of glycerol.

12. The process of claim 11 wherein the transition metal catalyst is supported on activated carbon and produced before step (a) by reduction with hydrogen of a passivated transition metal catalyst.

13. The process of claim 12 wherein the transition metal catalyst is selected from the group consisting of activated Ni/Re and Ru.

14. The process of claim 11 wherein the alkanol is selected from the group consisting of ethanol, isopropanol and tert-butanol alcohol.

15. The process of claim 11 wherein the alkali metal base is selected from the group consisting of sodium hydroxide, sodium bicarbonate, potassium hydroxide, potassium hydrogen carbonate and mixtures thereof.

16. The process of claim 11 wherein the alkali metal base is sodium hydroxide at a concentration of between about 0.1 and 1.0 M per mole of glycerol.

17. The process of claim 11 wherein the alkali metal base is potassium hydroxide at a concentration of between about 0.1 and 1.0 M per mole of glycerol.

18. The process of claim 11 wherein the catalyst is ruthenium metal as a sponge.

19. The process of claim 11 wherein the ether is dioxane.

20. The process of claim 11 wherein the reaction progresses over a time period between 4 to 6 hours.

21. The process of claim 11 wherein the reaction progresses at a temperature of 200° C. and a pressure of 1000 psig of $H_2$.

22. The process of claim 11 wherein the catalyst is Ni/Re provided at a quantity of 0.5 g supported on Carbon.

23. The process of claim 11 wherein the reaction progresses over conditions of temperature of 200° C., 1000 psig of $H_2$, using 0.5 g Ni/Re catalyst, 0.1M KOH, and 1.0M glycerol.

24. The process of claim 11 wherein the process further comprises adding 1.5 g of water to enhance KOH solubility.

25. The process of claim 1 wherein the reaction mixture is initially free from water prior to reacting the reaction mixture.

26. A process for the preparation of a composition comprising propylene glycol from glycerol which comprises:

(a) reacting a reaction mixture in a closed reaction vessel at a temperature between about 180° C. and 220° C. and at a pressure between about 800 and 1500 psig, the reaction mixture comprising: glycerol, a hydrogen activated transition metal catalyst, hydrogen, a solvent, and an alkali metal base;

(b) optionally separating the composition comprising the propylene glycol from the reaction mixture; and wherein the propylene glycol is produced at a selectivity ratio of propylene glycol to ethylene glycol from about 1.6:1 to about 11:1.

27. A process for the preparation of a composition comprising propylene glycol from glycerol which comprises:

(a) providing a reaction mixture consisting essentially of: glycerol, a hydrogen activated transition metal catalyst, hydrogen, a solvent selected from the group consisting of an alkanol containing 1 to 8 carbon atoms, an ether of the alkanol containing 1 to 8 carbon atoms, and mixtures thereof, and an alkali metal base to produce the composition comprising propylene glycol;

(b) reacting the reaction mixture in a closed reaction vessel at a temperature between about 180° C. and 220° C. and at a pressure between about 800 and 1500 psig;

(c) optionally separating the composition comprising the propylene glycol from the reaction mixture; and wherein the propylene glycol is produced with at least a 50% molar conversion of glycerol.

* * * * *

UNITED STATES PATENT AND TRADEMARK OFFICE
CERTIFICATE OF CORRECTION

| | | |
|---|---|---|
| PATENT NO. | : 7,619,124 B2 | Page 1 of 1 |
| APPLICATION NO. | : 12/079659 | |
| DATED | : November 17, 2009 | |
| INVENTOR(S) | : Miller et al. | |

It is certified that error appears in the above-identified patent and that said Letters Patent is hereby corrected as shown below:

Column 12, line 29, Claim 1, "from the reaction" should be --from the reaction mixture--.

Column 13, line 8, Claim 11, "from the reaction" should be --from the reaction mixture--.

Signed and Sealed this

Sixteenth Day of March, 2010

David J. Kappos
*Director of the United States Patent and Trademark Office*